United States Patent
Egnelöv

(10) Patent No.: US 8,398,675 B2
(45) Date of Patent: Mar. 19, 2013

(54) ABSORBABLE MEDICAL SEALING DEVICE WITH RETAINING ASSEMBLY HAVING AT LEAST TWO LOOPS

(75) Inventor: Per Egnelöv, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 637 days.

(21) Appl. No.: 10/280,086

(22) Filed: Oct. 25, 2002

(65) Prior Publication Data

US 2004/0093025 A1    May 13, 2004

(51) Int. Cl.
A61B 17/08  (2006.01)
(52) U.S. Cl. .................... 606/213; 606/215; 606/232
(58) Field of Classification Search ............ 128/887; 606/151, 153, 154, 157, 158, 213, 215, 216, 606/217, 220, 232, 159
See application file for complete search history.

(56) References Cited

U.S. PATENT DOCUMENTS

| 4,852,568 | A |   | 8/1989  | Kensey |        |
|-----------|---|---|---------|--------|--------|
| 4,917,089 | A |   | 4/1990  | Sideris |       |
| 5,021,059 | A | * | 6/1991  | Kensey et al. | 606/213 |
| 5,171,259 | A |   | 12/1992 | Inoue  |        |
| 5,350,399 | A |   | 9/1994  | Erlebacher et al. | |
| 5,383,904 | A | * | 1/1995  | Totakura et al. | 606/228 |
| 5,549,633 | A | * | 8/1996  | Evans et al. | 606/139 |
| 5,620,461 | A | * | 4/1997  | Muijs Van De Moer et al. | 606/213 |
| 5,700,277 | A | * | 12/1997 | Nash et al. | 606/213 |
| 5,861,004 | A |   | 1/1999  | Kensey et al. | |
| 6,159,234 | A | * | 12/2000 | Bonutti et al. | 606/232 |
| 6,383,201 | B1 |  | 5/2002  | Dong   |        |
| 6,506,197 | B1 | * | 1/2003 | Rollero et al. | 606/148 |
| 7,041,713 | B2 | * | 5/2006 | Yamauchi et al. | 523/113 |
| 2002/0019648 | A1 | | 2/2002 | Akerfeldt et al. | |
| 2002/0095179 | A1 | | 7/2002 | Tenerz et al. | |

FOREIGN PATENT DOCUMENTS

| DE | 200 09 815 U1 | 8/2000 |
| EP | 0 766 947 A2 | 4/1997 |
| EP | 0 894 475 A1 | 2/1999 |
| EP | 0 474 752 B2 | 12/2000 |
| EP | 1 147 743 A1 | 10/2001 |
| EP | 1147743 A1 * | 10/2001 |
| EP | 1 159 919 A2 | 12/2001 |
| EP | 1 169 968 B1 | 1/2002 |
| WO | WO 01/40348 A2 | 6/2001 |
| WO | WO 01/82990 * | 11/2001 |

OTHER PUBLICATIONS

U.S. Appl. No. 10/124,725, filed Apr. 18, 2002, Akerfeldt et al.
U.S. Appl. No. 09/704,726, filed Nov. 3, 2000, Akerfeldt et al.

* cited by examiner

*Primary Examiner* — Tuan V Nguyen
(74) *Attorney, Agent, or Firm* — Foley & Lardner LLP

(57) ABSTRACT

A device having an inner seal and a retaining assembly seals a puncture in a blood vessel. The inner seal is placed inside the blood vessel and seals the puncture by contacting the inner surface wall of the blood vessel. The retaining assembly has at least two loops which engage the inner seal. Each loop may remain in substantial contact with the inner seal for substantially 360 degrees of the travel of each loop. The at least two loops may lie in a plane which is parallel to both the major axis of the inner seal and a folding axis. A locking member may be slid along the retaining assembly so as to contact the outer surface wall of the blood vessel.

33 Claims, 3 Drawing Sheets

ABSORBABLE MEDICAL SEALING DEVICE WITH RETAINING ASSEMBLY HAVING AT LEAST TWO LOOPS

FIELD OF THE INVENTION

The present invention relates generally to the field of sealing devices for the sealing of a percutaneous puncture in a vessel. The invention relates particularly to an absorbable or bioabsorbable sealing device comprising an intra-arterial sealing member being provided with a number of through holes for a retaining member, wherein the retaining member is threaded through the through holes in at least two loops such that the risk that the retaining member ruptures through the intra-arterial sealing member is minimized.

BACKGROUND OF THE INVENTION

During certain types of medical surgery or treatment, an introducer is used to access the vascular system of a patient. The introducer is inserted through the wall of a blood vessel in order to obtain access to the vascular system, and may thereafter be used for guiding medical instruments such as catheters, guide wires and the like. After completion of the medical procedure, there will be an incision or a wound in the wall of the blood vessel corresponding to the size of the introducer. The bleeding from the wound, which is a result of such a surgical operation, can be stopped by applying direct pressure on the wound. However, applying direct pressure on the wound requires assistance of medical personnel and may also restrict the flow of blood through the vessel.

EP 766 947 B1 describes a haemostatic puncture device for sealing a percutaneous puncture. The main parts of this device are an anchoring means, a collagen foam acting as a sealing means, a filament means and a carrier means. The device uses an introducer or the like in order to guide the different parts to the puncture. The anchoring means, which is a narrow, rigid beam member, is introduced through the puncture to be inserted into the vessel. During the introduction, the anchoring means is in a longitudinal position in order to fit in the introducer. To function as an anchor, the anchoring means is manipulated in such a way that its end portions grip the inner edges of the puncture. The anchoring means is connected to the sealing means by the filament means in a pulley-like configuration. Thus, after the anchoring means has been put in place and the introducer has been withdrawn, the pulley-like configuration will pull the sealing means towards the puncture and eventually seal the puncture on the outside wall of the vessel. Thus, the collagen foam performs all the sealing, i.e. the puncture is only sealed on the outside wall of the vessel. The collagen foam is effective in stopping the flow of blood through the puncture wound, but the closure device according to EP 766 947 B1 has disadvantages. Besides the potential risk that the local tension applied to the edges of the puncture by the anchoring means may rupture the edges of the puncture, there is a potential risk that the tension in the filament means will cause the filament means to rupture through the anchoring means, thereby leaving the anchoring means loose inside the vessel. Furthermore, the use of a sealing device that seals on the outside of the vessel only enhances this potential problem, because an outer sealing requires a higher sealing force, i.e. a higher tension in the filament means, than a corresponding inner sealing.

Another sealing device is disclosed in U.S. Pat. No. 4,852,568. This device comprises a retraction filament fixedly secured to a plug means to be introduced into the vessel by an introducer means. When the plug means, which is made of a material being absorbable by the body, has been introduced into the vessel, the retraction filament is pulled until the engagement surface of the plug means is in intimate engagement with the interior of the artery wall. In order to hold the closure in place, the filament is held taut and is secured in position on the patient's skin, such as by use of a strip of conventional tape. Unlike the sealing means disclosed in EP 766 947 B1, the plug means according to U.S. Pat. No. 4,852,568 seals the puncture on the inside of the vessel wall. However, the risk that the fastening means, in this case a filament such as a very thin thread, which must be pulled with considerable force and which is then left tightened for a time period being as long as several days or even weeks, ruptures through the plug means is still present. Furthermore, the risk may be enhanced by the fact that the plug means according to U.S. Pat. No. 4,852,568 is made of an absorbable (e.g. biodegradable) material that also is resilient (a preferred material according to U.S. Pat. No. 4,852,568 is Gelfoam, a porous, absorbable gelatine sold by Johnson & Johnson, Inc.) since such materials usually are known to have low rupture strength.

Through U.S. Pat. No. 5,350,399 is disclosed another sealing device for sealing a puncture in the wall of a blood vessel. This sealing device comprises an intra-arterial occluder and an extra-arterial occluder, which, in a sealing position, are held together by a guide means being integral with and extending centrally from the intra-arterial occluder. According to U.S. Pat. No. 5,350,399, the guide means, which can be in the form of an elongated flexible wire, as well as the occluders can be made from a bioabsorbable material. Further, each occluder is formed of a material and has a shape so as to be circumferentially collapsible from a normal position, and should be resiliently expandable from the collapsed state to the normal position. As stated above, bioabsorbable materials having these properties are often characterized by having low rupture strength, and the risk that the fastening means, in this case in the form of a guide means, will rupture through the intra-arterial occluder is still present.

The problem that a retaining member ruptures through an intra-arterial sealing member is also recognized in EP 474 752 B2, whose aim is to provide an occlusion assembly with which it is possible to apply more tension to the retaining element. The occlusion assembly according to EP 474 752 B2 comprises an occlusion member to be fitted against the inner wall of a vessel, a locking member to be fitted against the outer vessel wall, and a retaining element connecting the occlusion member and the locking member, so that, in use, the portion of the retaining element which passes through the wall of the blood vessel between the locking member and the occlusion member is in tension. Although no numbers for the size of this tension are given in the application, it can be assumed—both from the above stated aim of the invention and from the fact that the occlusion assembly according to EP 474 752 B2 seals a puncture in the wall of a vessel by clamping the vessel wall between the occlusion member and the locking member—that there is a considerable tension applied to the retaining element, with the accompanying risk for rupture of the occlusion member.

In this context, it should be noted that the problem that an inner seal, i.e. a sealing member designed to be positioned against the inner wall of a blood vessel, will come loose in the artery has severe implications both on long and short terms. If the retaining means ruptures through the inner seal during the introduction or shortly after its introduction, i.e. before haemostasis is obtained, the immediate problem is, of course, to stop the flow of blood through the puncture wound. For this incident, when a sealing operation is carried out using this type of intra-arterial occluder, a device for applying external compression pressure on the puncture site is often kept prepared as a precaution. If, however, the retaining means ruptures through the inner seal when haemostasis already is obtained, the problem is that the inner seal can follow the flow of blood to a position where the artery is so narrow that the inner seal occludes the blood vessel, which may necessitate amputation of the part of the body in which the inner seal has got stuck. Having in mind that it normally takes several months before the body actually absorbs arterial sealing devices being made of an absorbable material, it is easy to realize that the long-term requirements regarding the rupture strength of such sealing devices are quite severe.

It should also be noted that a requirement for an intra-arterial sealing device is that it is resilient, since it usually has to be folded, collapsed or in some other way deformed in order to fit in some kind of introducer means before the introduction through the puncture hole and into the vessel. When positioned inside the vessel, the sealing device is unfolded or expanded so as to seal the puncture in the vessel wall. In other words, the diameter of the sealing device must be smaller than the diameter of the puncture hole in the introduction phase, whereas the diameter of the sealing device must be larger than the diameter of the puncture hole in the sealing phase. Generally speaking, the problem is that absorbable (e.g. biodegradable) materials having these properties, i.e. being characterized by having a low modulus, usually also are characterized by having low rupture strength. The rupture strength referred to herein relates to the force needed to displace an implanted object, which is fixed by some fastening or retaining means, such as sutures, filaments, screws or other fasteners or retainers used to fix the object in position relative to the surrounding soft or hard tissue, or the force needed to displace the fastening or retaining means once stitched through the implanted object. The rupture strength of a material is related to the modulus (commonly also referred to as the elastic modulus or Young's modulus) of the material, so that a low modulus material is characterized by having low rupture strength. A high modulus material has a higher resistance to force.

Additional general background is set forth in U.S. patent application Publication Ser. No. 2002/0,019,648A1, whose entire contents are incorporated herein by reference.

SUMMARY OF THE INVENTION

An object of the present invention is therefore to provide an improved arterial sealing device that provides safe sealing of a percutaneous puncture and at the same time reduces the risk that a retaining means connected to an inner seal ruptures through the absorbable material such that the inner seal comes loose inside the artery.

This object is partly achieved by providing a sealing device comprising a locking member, an inner seal, which is provided with through holes, and a retaining member, wherein the retaining member is connected to the inner seal by means of an improved way of threading the retaining member through the holes in the inner seal. A similar way of threading a retaining member is described in EP 1 159 919 A2, which, however, is addressing a completely different problem, namely to provide safe unfolding of a folded, two-part sealing device.

The present invention is an improvement of the sealing devices disclosed in EP 1 147 743 A1 and EP 1 169 968 B1, which are assigned to the present assignee, and the reader is referred to the latter for more details regarding peripheral equipment, such as the introducer, or the method with which the sealing device is positioned at a vessel wall in order to seal a puncture therein. The entire contents of these two documents are incorporated herein by reference.

According to one aspect of the invention, the invention provides a device for sealing a puncture in a blood vessel, comprising an inner seal configured to be placed inside a blood vessel and to seal a puncture in the blood vessel by contacting an inner surface wall of the blood vessel, and a retaining assembly having at least two loops which engage the inner seal.

According to another aspect of the invention, the invention provides a device for sealing a puncture in a blood vessel comprising an inner seal configured to be placed inside a blood vessel and to seal a puncture in a blood vessel by contacting an inner surface of the blood vessel essentially without deforming the blood vessel wall.

According to another aspect of the invention, the invention provides a sealing device comprising an inner seal adapted to be fitted against the inner wall of a vessel, a locking member to be fitted against the outer wall of the vessel, and a retaining member connecting the inner seal and the locking member and being attached to the inner seal with at least two loops such that the strain on the inner seal is reduced, which, in turn, reduces the risk that the retaining member ruptures through the inner seal.

According to another aspect of the invention, the invention provides a device for sealing a puncture in a blood vessel, comprising an inner seal configured to be placed inside a blood vessel and to seal a puncture in the blood vessel, and a retaining assembly having at least two loops which engage the inner seal.

In one preferred embodiment, the inner seal has such a shape that it adapts to the surface of the inner vessel wall, so that an efficient sealing is achieved with a minimum of tension being applied to the retaining member, thereby further reducing the risk that the retaining member ruptures through the inner seal.

In a further embodiment, a locking member has such a shape that it can act as an outer seal in the event that the inner seal should not seal the puncture properly.

DETAILED DESCRIPTION OF THE PREFERRED EMBODIMENTS

In order to effectively seal an arterial puncture wound, an absorbable sealing device for intra-arterial (or extra-arterial) sealing should preferably be made of a material that is characterized by being soft and flexible, i.e. the material is characterized by having a low modulus. As discussed above, it is also important that the device be deformable to fit in the introducer and also be capable of unfolding or expanding in the blood vessel. Such materials can be made from natural biopolymers or from synthetic materials that degrade into harmless components within a living tissue. Examples of materials may be various natural biopolymers, pure or chemically manipulated, based on alginic acid, hyalauronic acid or chitosan. Examples of soft and flexible synthetic absorbable polymers are aliphatic polyurethanes, polyphospazenes and polyorthoesters, and those polymers made from glycolide, lactide, caprolactone, trimethylene carbonate, butyrolactone, 1,4-dioxan-2-one or 1,5-dioxepan-2-one. Yet another way to achieve a soft and flexible material is the use of plasticizers to bring down the glass transition temperature of the material in question. Such suitable materials have an elastic modulus that ranges from 50 to 120 MPa, and more preferably from 60 to 80 MPa.

As described above, soft and flexible absorbable materials normally have a low rupture strength, which, in turn, means that there is a potential risk that a retaining means, such as a multifilament or a suture, is torn lose by rupturing through a sealing member being made from such materials. During the implantation procedure, the doctor needs to feel that the sealing member is pulled in close apposition to the vessel wall. During this procedure, the doctor needs to pull with some force, which is applied with great individual variability and which will be transmitted through the retaining means and act on the sealing member. With the conventional way of threading the retaining member, e.g. through two through holes in an intra-arterial sealing member, there is therefore a potential risk that the retaining member saws its way through the material in the sealing member between the two through holes, thereby leaving the sealing member loose inside the vessel. In order to overcome this potentially severe problem, a new way of threading the retaining member is proposed, as set forth below.

Further, when correctly positioned against the inner wall of a vessel, the intra-arterial sealing member according to the present invention has the ability to seal a puncture hole with a minimum of tension being applied in the retaining member. This is an advantage since the smaller the tension in the retaining member, the less the risk that the retaining means ruptures through the intra-arterial sealing member.

Figure 1:
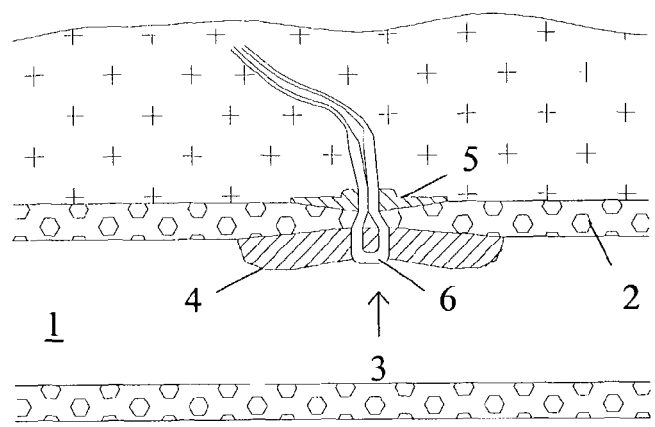
FIG. 1 is a cross-sectional view of a previously proposed wound closure device positioned around a puncture hole in a vessel.

In FIG. 1 is illustrated a portion of a vessel 1 in a living body, such as the femoral artery. A puncture has been made through the vessel wall 2, thereby creating an opening, which has to be occluded after the treatment that made the puncture necessary. In FIG. 1, a previously proposed wound closure device 3 has been implanted to close the puncture wound. The wound closure device 3 comprises an intra-arterial sealing member 4, which is positioned against the inner surface of the vessel wall 2, and an extra-arterial sealing member 5, which is positioned against the outer surface of the vessel wall 2. The wound closure device 3 comprises also a fastening or retaining means 6 in the form of a multifilament 6, which holds the intra-arterial and extra-arterial sealing members 4, 5 together by means of friction locking. As is usual in this type of device, this wound closure device 3 seals the puncture in the vessel 1 by clamping the vessel wall 2 between the intra-arterial sealing member 4 and the extra-arterial sealing member 5.

Figure 2:
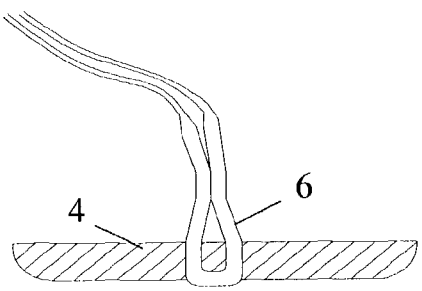
FIG. 2 shows a cross-section of the retaining means and the intra-arterial sealing member of FIG. 1.

As is best seen in FIG. 2, the intra-arterial sealing member 4 comprises also two through holes, through which the multifilament 6 is threaded in a single loop. With this device, there is therefore a relatively small amount of material between the two through holes, which, as mentioned above, implies that there is a risk that the multifilament 6 ruptures through the intra-arterial sealing member 4 because the multifilament 6 concentrates force on member 4 over a small area.

Figure 3:
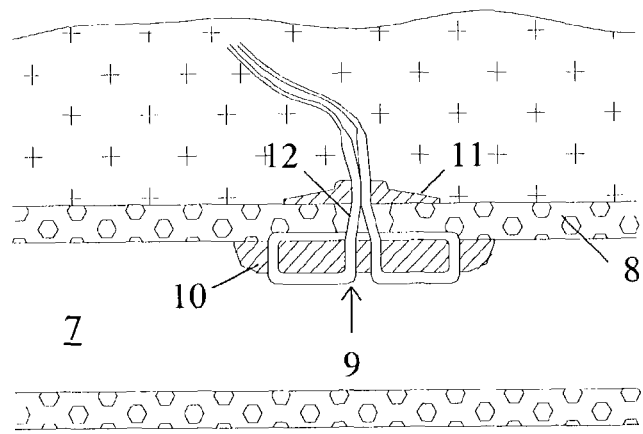
FIG. 3 is a cross-sectional view of an inventive sealing device implanted in a sealing position around a puncture in the wall of a vessel.
Figure 5:
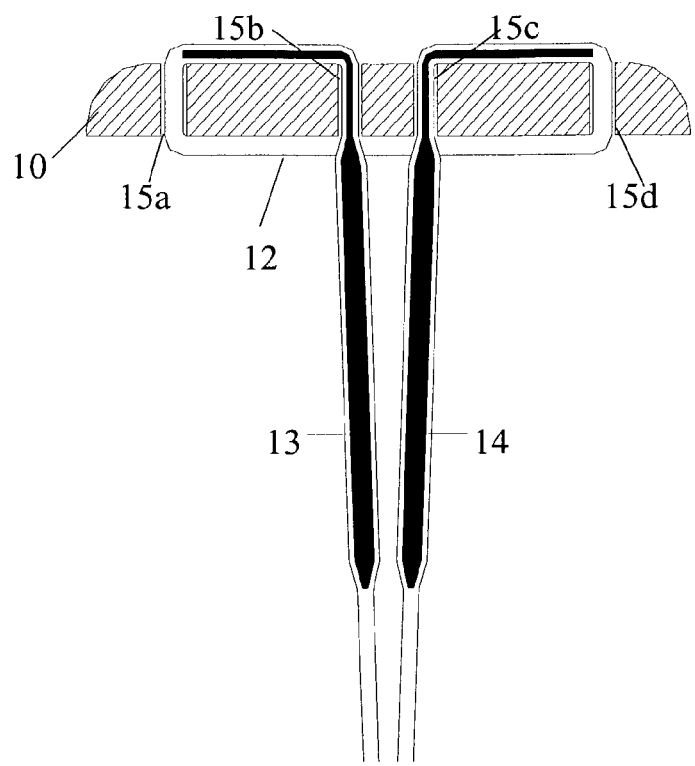
FIG. 5 shows a cross-section of a retaining member and the inner seal of FIG. 4.

FIG. 3 illustrates the same type of puncture through the wall 8 of a vessel 7. In this case, a sealing device 9 according to the present invention has been positioned to close the puncture wound in the vessel wall 8. The sealing device 9 comprises basically three separate parts, namely an inner seal 10, which is adapted to be positioned against the inner surface of the vessel wall 8, a locking member 11, which is to be positioned against the outer surface of the vessel wall 8, and a retaining assembly in the form of a retaining member 12. These components are made from bioabsorbable materials. In this embodiment, the retaining member 12 is in the form of a multifilament 12, which extends through the puncture hole and connects the inner seal 10 with the locking member 11. The retaining member can be any other type of thread such as a suture. As is seen in FIG. 5, the retaining member 12 comprises also two elongated members 13, 14, which are inserted in the distal portion of the multifilament 12. The function of these elongated members 13, 14 is to provide a secure locking for the locking member 11 by means of friction. During implantation of the sealing device 9, when the inner seal 10 has been pulled in close apposition to the inner surface of the vessel wall 8, the locking member 11 can easily slide along the thin proximal portion of the multifilament 12 until it is pushed up on and along the thicker distal portion of the multifilament 12 and into contact with the outer surface of the vessel wall 8, where it remains securely seated by the friction locking in order to hold the inner seal 10 in place.

Figure 6:
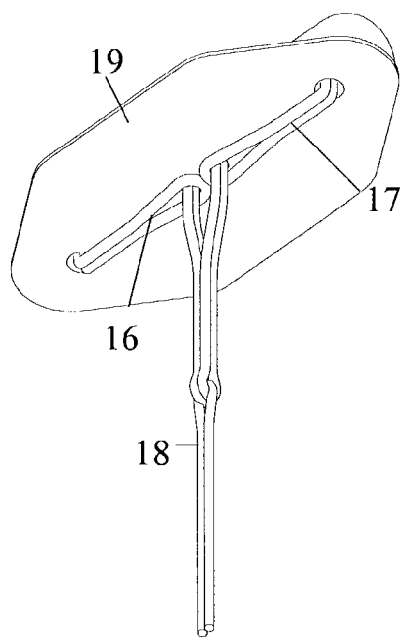
FIG. 6 illustrates an alternative embodiment in which two retaining members are connected to an inner seal.
Figure 7:
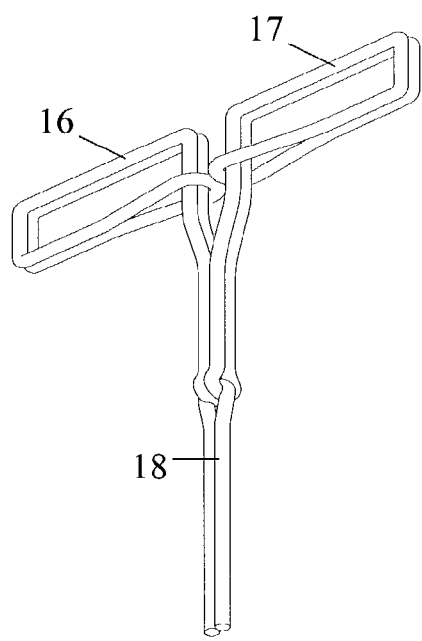
FIG. 7 illustrates the threading of the retaining members of FIG. 6.

Instead of inserting elongated members into a multifilament, it is also possible to provide the extra thickness at the distal end of a multifilament, and thereby the friction locking for the locking member, by other means. A multifilament could, for example, be coated or dressed with some extra material, so that the extra thickness is provided from the outside rather than from the inside of the multifilament. An alternative locking arrangement is shown in FIG. 6 and FIG. 7, wherein, at the distal end, the multifilament is doubled up to provide a friction lock.

Further details of locking members, materials and other relevant information is set forth in U.S. patent application Ser. No. 10/124,725, filed Apr. 18, 2002; U.S. patent application Ser. No. 10/042,247, filed Jan. 11, 2002; U.S. patent application Ser. No. 09/704,726, filed Nov. 3, 2000; and PCT Publication No. WO 01/40348A2. The entire contents of all of these documents are incorporated herein by reference.

As can be seen from FIG. 3, the vessel wall 8 is much less deformed than the vessel wall 2 of FIG. 1. This feature reflects the fact that the sealing device 9 preferably seals the puncture hole by holding the inner seal 10 in intimate engagement with the inner surface of the vessel wall 8, or, in other words, there is only a minimal amount of tension applied in the filament 12. This way of sealing a puncture hole is in contrast to the prior art sealing devices, wherein a puncture hole is sealed by clamping the vessel wall between an intra-arterial sealing member and an extra-arterial sealing member. The present way of sealing the puncture hole is advantageous in that less tension has to be applied in the multifilament 12, which, in turn, means that there is less risk that the multifilament 12 ruptures through the inner seal 10. This way of sealing a puncture hole requires that the inner seal 10 to a large extent has the ability to adapt to the structure of the inner surface of the vessel wall 8. The characteristics of the inner seal 10 will be described in more detail below.

Figure 4:
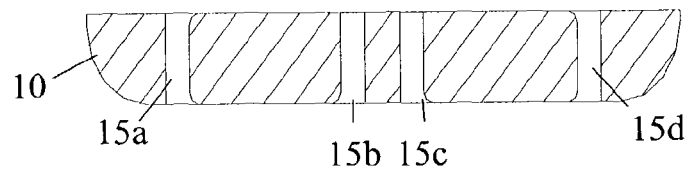
FIG. 4 shows a cross-section of an inner seal according to the present invention.

The cross-section of the inner seal 10 is shown in FIG. 4, where it can be seen that the inner seal 10 also comprises in total four through holes, two outer holes 15*a* and 15*d* and two inner holes 15*b* and 15*c*. As already is indicated in FIG. 3 and more fully described in conjunction with FIG. 5 below, the multifilament 12 is threaded through these four through holes 15*a-d* in such a way that the strain on the inner seal 10 is reduced in comparison with the conventional way of threading a retaining member through, for example, only one or two through holes.

The way in which the multifilament 12 is threaded through the four through holes 15*a-d* is illustrated in FIG. 5. As can be seen from the figure, the multifilament 12 is threaded such that the ends of the multifilament 12 are threaded through the two outer holes 15*a* and 15*d*, from the under side of the inner seal 10 to its upper side, and the ends of the multifilament 12 are then threaded through the two inner holes 15*b* and 15*c*, from the upper side of the inner seal 10 to its under side, so that two separate loops are formed. Herein, the under side of the inner seal 10 is defined as the side of the inner seal 10 that is to be positioned in engagement with the vessel wall, whereas the upper side of the inner seal 10 is the side that will face the interior of the vessel. A perhaps simpler way to describe the threading of the multifilament 12 is to note that the threaded multifilament 12 is characterized by having two separate portions on the upper side of the inner seal 10, while there is only one portion on the under side of the inner seal 10.

It could also be mentioned that it is possible to let the two inner holes 15*b* and 15*c* be merged into a single larger hole, which is positioned in the centre of the inner seal and which receives both ends of the multifilament. In principle, it is also possible to provide an inner seal with more than four holes, so that a retaining member is threaded in more than two loops. Yet another way to achieve the same effect, i.e. to reduce the strain on the inner seal, would be to use more than one retaining member. An example of the latter is illustrated in FIG. 6 and FIG. 7, where two retaining members 16, 17 have been threaded through an inner seal 19 such that two separate loops are formed. Outside of the inner seal 19, the two retaining members 16, 17 are connected by a third retaining member 18, so that a configuration having the same function as the combination of the multifilament 12 and the elongated members 13, 14 shown in FIG. 5 is formed. As already has been mentioned, there are different ways of providing the friction locking, i.e. of arranging the retaining assembly. However, a common requirement is that a central part of the retaining assembly, i.e. the part that extends through the puncture hole, occupies a diameter that is less than or equal to the diameter of the puncture hole, so that the edges of the puncture hole are not damaged by the retaining member(s). This requirement is valid also for the previously proposed retaining assemblies, the advantage with the new threading of the retaining member being that the outer through holes are positioned such that the distance between them is larger than the diameter of the puncture hole, thereby allowing the retaining member to enclose more material so that the risk that the retaining member ruptures through the inner seal is significantly reduced in comparison with the previously proposed sealing devices.

From a comparison of the intra-arterial sealing member 4 illustrated in FIG. 2 and the inner seal 10 illustrated in FIG. 5 it should now be possible to fully appreciate a special advantage of the present invention. With the present design of the inner seal 10 and the improved threading of the retaining member 12, the force from the retaining element 12 that acts on the inner seal 10 is spread out over an area that is much larger than the corresponding area of the sealing member 4. Consequently, the risk that the retaining element 12 ruptures through the inner seal 10 has been significantly reduced. Furthermore, the two loops of the retaining member 12 enclose more material than does the single loop, which means that the retaining element 12 has to saw its way through more material.

Figure 8:
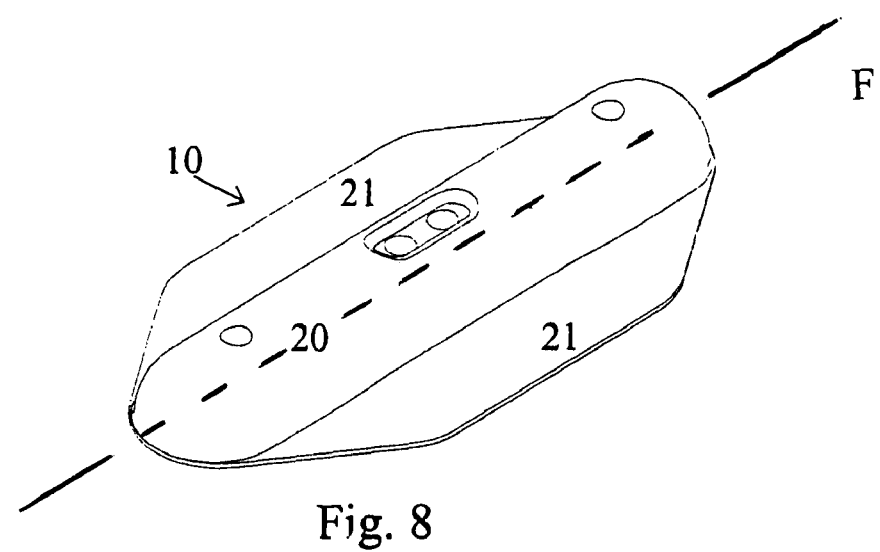
FIG. 8 is a schematic view of the inner seal of FIG. 3.

As mentioned above, to seal a puncture hole with only a minimum of tension being applied in a retaining member puts special requirements on an inner seal, i.e. it has to be resilient and soft enough to adapt to the surface of the vessel wall. FIG. 8 shows the inner seal 10 according to the present invention. As can be seen from the figure, the inner seal 10 includes a central, elongated portion 20 surrounded by a rim portion 21. The central portion 20, together with the improved way of threading the retaining member, provides the inner seal 10 with the necessary stiffness and rupture strength, while the comparatively thinner rim portion 21 provides the resilience which is necessary for the inner seal to adapt to the surface of the vessel wall so as to seal a puncture hole without actually clamping the vessel wall between the inner seal 10 and the locking member 11. In an introducer as described in the 2002/0019648 and EP 1 169 968 (cited above) prior to placement in the blood vessel, seal 10 is folded along a folding axis F and placed in an introducer.

Before further describing the sealing device according to the present invention, a few words could be said about the tension in the retaining member and the way that the inner seal seals a puncture hole in the wall of a vessel. The tension in a retainer, which extends from an inner member positioned against the inner vessel wall, through a puncture hole in the vessel wall and to an outer member positioned against the outer vessel wall, can range continuously from zero to a large value. With a resilient inner member which adapts perfectly to the surface of the inner vessel wall, it is, at least theoretically, possible to seal the puncture hole without applying any tension in the retainer, i.e. when the length of the retainer between the inner member and the outer member matches exactly the thickness of the vessel wall. The other extreme, i.e. a large tension in the retainer, corresponds to the case when the puncture hole is sealed by clamping the vessel wall between the inner member and the outer member. In the latter case, it is neither necessary nor important that the inner member is resilient, since the sealing is achieved by deformation of the vessel wall, i.e. the vessel wall adapts to the inner member in such a way that the fluid inside the vessel cannot penetrate into the puncture hole.

From the above, it should be clear that the sealing device according to the present invention preferably belongs to a class of sealing devices comprising an inner seal, which seals a puncture by adapting to the inner surface of the vessel wall, and a locking member, which is positioned at the outer vessel wall and whose primary function is to hold the inner seal in place. With such a sealing device, the tension in a retaining member can be reduced to a minimum, which is in contrast to sealing devices that seal a puncture wound by clamping and deforming the vessel wall between an inner member and an outer member. A minimal tension could therefore be defined as the amount of the tension required to make the inner seal to adapt to the inner surface of the vessel wall. For example, a small amount of tension in the retaining member is required to unfold the thin rim portion of the inner seal according to the present invention, since the inner seal, before the introduction, has been compressed inside an introducer. Further, if only a minimal tension is going to be applied, the friction locking of the locking member has to be continuously variable, i.e. the locking member has to be continuously movable along the distal portion of the retaining member. This is, for example, in contrast to devices in which an outer member is secured by saw teeth provided on a retaining member. With the present invention, the tension in the retaining member, immediately after completion of the positioning of the inner seal and the locking member, is approximately less than 1 N and approaches zero when the sealing device has been in place for a while. Here, one has to remember that, as is usual within the art, the sealing device according to the present invention preferably is made from an absorbable material that slowly degrades inside the body. This means that the sealing device, during its lifetime, will be in different states of dissolution or degradation, and the risk that the retaining member ruptures through the inner seal would, without the improved threading of the retaining member, still be present even though the tension in the retaining member is very small. In other words, the improved way of threading the retaining member and the small tension in the retaining member, which is due in part to the resilient rim portion of the inner seal, are complementary, which is not to say that they can not perform their functions independently of each other.

Figure 9:
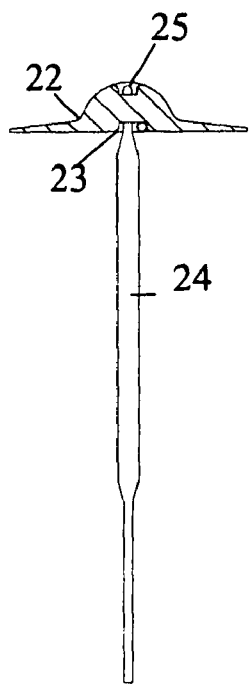
FIG. 9 is a cross-sectional end view of one embodiment of the inner seal according to the present invention.
Figure 10:
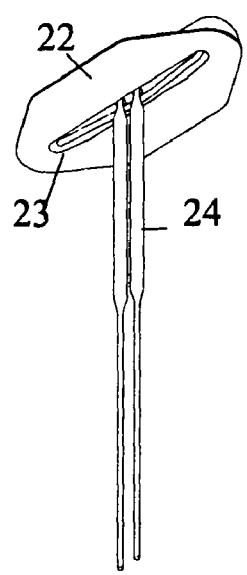
FIG. 10 is a schematic view of the under side of the inner seal of FIG. 9.

For the ability of the inner seal to adapt to the surface structure of the vessel wall, it may be an advantage that the under side of the inner seal is flat, i.e. that there are no elevated parts. Apparently, this is not the case for the combination of an inner seal and retaining member shown in FIG. 3 and FIG. 5, where the thickness of the multifilament 12 has been increased for the sake of clarity. FIG. 9 shows an end view of an alternative embodiment of an inner seal 22 according to the present invention. As can be seen from FIG. 9 and also from FIG. 10, the under side of the inner seal 22 is provided with a longitudinal recess 23, in which a loop of a retaining member 24 is placed so that the periphery of the retaining member 24 is in level with the under side of the inner seal 22. This feature facilitates the ability of the inner seal 22 to adapt to the surface of a vessel wall, since there are no parts projecting out from the under side of the inner seal 22.

Figure 11:
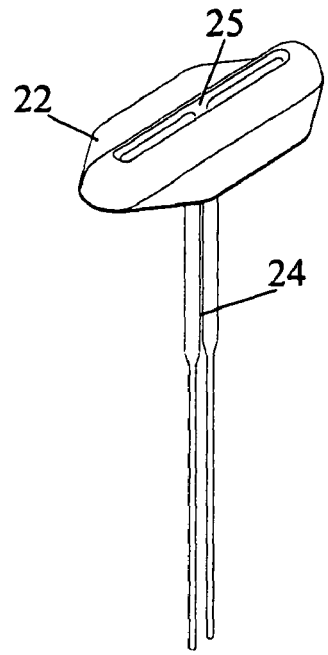
FIG. 11 is a schematic view of the upper side of the inner seal of FIG. 9.

As can be seen from FIG. 9 and also from FIG. 11, the upper side of the inner seal 22 is also provided with a longitudinal recess 25, in which the two loops (as was described in conjunction with FIG. 5) of the retaining member 24 are placed so that the periphery of the retaining member 24 is in level with the upper side of the inner seal 22. With this positioning of the retaining member 24, the inner seal 22 exhibits a flat upper side, which obstructs the fluid flow in a vessel less than an upper side provided with a projecting retaining member.

The provision of one or both of the recesses 23, 25 is optional, and the importance of embedding the retaining member in, for example, a recess in the under side of the inner seal depends on the specific design and particular choice of material for the inner seal in question. Thus, if the material from which the inner seal is made is soft and resilient enough, it may not be necessary to provide the above-mentioned recesses, but for other choices of material and other designs it might be advantageous.

Figure 12:
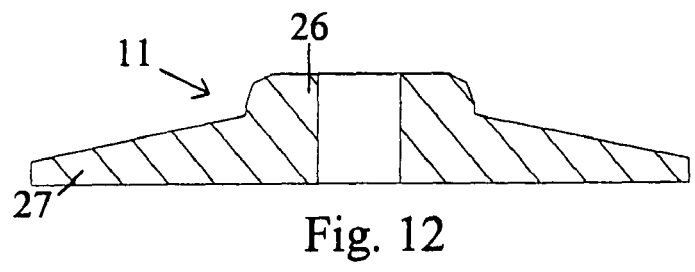
FIG. 12 shows a cross-section of a locking member according to the present invention.

In FIG. 12 is shown a cross-section of the locking member 11 shown in FIG. 3. From the above-mentioned fact that the primary function of the locking member 11 is to hold the inner seal 10 seated against the inner surface of a vessel wall, it follows that the locking member 11 in principle could have any shape, as long as the requirements arising from the dimensions of an introducer and the size of the puncture hole are fulfilled. However, if, for some reason, the inner seal 10 does not seal the puncture properly, so that some fluid from the interior of the vessel penetrates into the puncture hole, the locking member 11 should preferably have such a shape that it can act as an outer seal 11 and, if necessary, assist in the sealing of the puncture. For that incident, the locking member 11 has basically the same structure as the inner seal 10, with a thick central portion 26 surrounded by a thin rim portion 27. The thicker central portion 26 provides the necessary mechanical strength for a secure friction locking between the locking member 11 and the retaining member 12, while the thinner rim portion 27 provides the resilience which is necessary for the ability of the locking member 11 to adapt to the outer surface of the vessel wall and thereby, if necessary, seal the puncture from the outside of the vessel wall.

The improved way of threading can also be used in a situation where there exists a large tension in the retaining assembly, even if the vessel wall is deformed by this tension, because the improved way of threading minimizes the risk that the retaining assembly will rupture or saw through the inner seal.

Although the present invention has been described with reference to specific embodiments, also shown in the appended drawings, it will be apparent for those skilled in the art that many variations and modifications can be done within the scope of the invention as described in the specification and defined with reference to the following claims.

What is claimed is:

1. A device for sealing a puncture in a blood vessel, comprising:
    an inner seal configured to be placed inside the blood vessel and to seal the puncture in the blood vessel by contacting an inner surface wall of the blood vessel, the inner seal having a major axis along a largest dimension of the seal, wherein the inner seal is bioabsorbable;
    a retaining assembly having at least two loops which engage the inner seal such that each loop remains in substantial contact with the inner seal for substantially 360 degrees of travel of each loop, the at least two loops lying in a plane which is parallel to both the major axis and a folding axis; and
    a locking member configured to slide along the retaining assembly and contact an outer surface wall of the blood vessel.

2. A device as set forth in claim 1 wherein the retaining assembly is configured to retain the inner seal in contact with the inner surface wall of the blood vessel with a minimal tension being applied in the retaining assembly.

3. A device as set forth in claim 1, wherein the retaining assembly is configured to retain the inner seal in contact with the inner surface wall of the blood vessel with less than 1 N tension in the retaining assembly.

4. A device as set forth in claim 1, wherein the locking member is configured to seal the puncture from outside the blood vessel.

5. A device as set forth in claim 1, wherein the retaining assembly comprises a thread.

6. A device as set forth in claim 5, wherein the inner seal comprises at least three holes, wherein each end of the thread is threaded from an under side of the inner seal to an upper side of the inner seal via two outermost holes and then from the upper side to the under side via at least one innermost hole to form the at least two loops.

7. A device as set forth in claim 5, wherein the thread is threaded through the inner seal such that the thread has two separate portions on an upper side of the inner seal and one integral portion on an under side of the inner seal.

8. A device as set forth in claim 1, wherein the inner seal comprises at least three holes through which the retaining assembly extends.

9. A device as set forth in claim 8, wherein a distance between two outermost holes of said at least three holes is greater than or equal to a size of said puncture.

10. A device as set forth in claim 1, wherein the retaining assembly comprises a multifilament and at least one elongated member inserted in a distal portion of the multifilament to make the multifilament thicker.

11. A device as set forth in claim 1, wherein the retaining assembly comprises one retaining member which forms both loops.

12. A device as set forth in claim 1, wherein the retaining assembly comprises a first retaining member which forms one of the two loops and a second retaining member which forms the other of the two loops.

13. A device as set forth in claim 12, further comprising a third retaining member to connect the first retaining member and the second retaining member.

14. A device as set forth in claim 1, wherein the inner seal comprises a thick central elongated portion at least partially surrounded by a thin rim portion.

15. A device as set forth in claim 1, wherein the locking member comprises a thick central portion at least partially surrounded by a thin rim portion.

16. A device as set forth in claim 1, wherein the retaining assembly comprises a thread which has been doubled up at least one time to make the thread thicker.

17. A device as set forth in claim 1, wherein the inner seal is configured to contact the inner surface wall of the blood vessel around the entire circumference of the puncture.

18. A device as set forth in claim 1, wherein the retaining assembly is bioabsorbable.

19. A device as set forth in claim 1, wherein the locking member is bioabsorbable.

20. A device as set forth in claim 1, wherein the retaining assembly is configured to retain the inner seal in contact with the inner surface wall of the blood vessel essentially without deforming the vessel wall.

21. A device as set forth in claim 1, wherein the retaining assembly comprises a thread whose distal end has been coated or dressed to make the distal end thicker.

22. A device as set forth in claim 1, wherein a diameter of the retaining assembly is increased at a distal end to friction lock the locking member and the retaining assembly.

23. A device as set forth in claim 1, wherein the inner seal is constructed of a bioabsorbable material having an elastic modulus from 50 to 120 MPa.

24. A device as set forth in claim 1, wherein the inner seal is constructed of a bioabsorbable material having an elastic modulus from 60 to 80 MPa.

25. A device for sealing a puncture in a blood vessel, comprising:
an inner seal configured to be placed inside the blood vessel and to seal the puncture in the blood vessel by contacting an inner surface wall of the blood vessel; and
a retaining assembly having at least two loops which engage the inner seal; and
wherein the inner seal comprises a recess in an under side of the inner seal to house at least a portion of the retaining assembly such that a periphery of the retaining assembly does not project from the under side.

26. A device for sealing a puncture in a blood vessel, comprising:
an inner seal configured to be placed inside the blood vessel and to seal the puncture in the blood vessel by contacting an inner surface wall of the blood vessel; and
a retaining assembly having at least two loops which engage the inner seal; and
wherein the inner seal comprises a recess in an upper side of the inner seal to house at least a portion of the retaining assembly such that a periphery of the retaining assembly does not project from the upper side.

27. A device for sealing a puncture in a blood vessel, comprising:
an inner sealing means, configured to be placed inside the blood vessel, for contacting an inner surface wall of the blood vessel and for thereby sealing the puncture in the blood vessel, the inner sealing means having a major axis along a largest dimension of the inner sealing means, wherein the inner sealing means is bioabsorbable;
a retaining means for forming at least two loops to engage the inner sealing means such that each loop remains in substantial contact with the inner sealing means for substantially 360 degrees of travel of each loop and such that force exerted by the retaining means on the inner sealing means is distributed over the inner sealing means, the at least two loops lying in a plane which is parallel to both the major axis and a folding axis; and
a locking means, configured to be placed inside the blood vessel, for contacting an outer surface wall of the blood vessel and for locking the inner seal means in place,
wherein the locking means is configured to slide along the retaining means.

28. A device as set forth in claim 1, wherein the inner seal is configured to seal the puncture by contacting the inner surface wall of the blood vessel essentially without deforming the blood vessel wall, and wherein the retaining assembly is configured to retain the inner seal such that force exerted by the retaining assembly on the inner seal is distributed over the inner seal over an area larger than said puncture.

29. A device as set forth in claim 28, wherein the inner seal is constructed of a bioabsorbable material having an elastic modulus from 50 to 120 MPa.

30. A device as set forth in claim 28, wherein the inner seal is constructed of a bioabsorbable material having an elastic modulus from 60 to 80 MPa.

31. A device as set forth in claim 28, wherein the retaining assembly is configured to retain the inner seal in contact with the inner surface of the blood vessel with minimal tension being applied in the retaining assembly.

32. A device for sealing a puncture in a blood vessel, comprising:
an inner seal configured to be placed inside the blood vessel and to seal the puncture in the blood vessel, the inner seal having a major axis along a largest dimension of the seal, wherein the inner seal is bioabsorbable;
a retaining assembly having at least two loops which engage the inner seal such that the retaining assembly enters and departs from the inner seal only at a central portion of the inner seal, the at least two loops lying in a plane which is parallel to both the major axis and a folding axis; and
a locking member configured to slide along the retaining assembly and contact an outer surface wall of the blood vessel.

33. A device as set forth in claim 32, wherein the at least two loops engage the inner seal such that each loop remains in substantial contact with the inner seal for substantially 360 degrees of travel of each loop.

* * * * *